United States Patent [19]

Babic

[11] 4,439,612

[45] Mar. 27, 1984

[54] PREPARATION FOR USE AS LUBE OIL ADDITIVES OF THIOUREAS CONTAINING N-POLYALKYLENEAMINO HYDROCARBYL SUCCINIMIDO GROUPS

[75] Inventor: Gary T. Babic, Beacon, N.Y.

[73] Assignee: Texaco Inc., White Plains, N.Y.

[21] Appl. No.: 189,514

[22] Filed: Sep. 22, 1980

[51] Int. Cl.³ .......................................... C07D 207/40
[52] U.S. Cl. ................... 548/546; 252/47.5; 252/49.8; 252/32.7 E; 252/32.7 HC
[58] Field of Search .............................. 260/326.5 FM

[56] References Cited

U.S. PATENT DOCUMENTS 3,200,107  8/1965  LeSuer .............................. 252/47.5
3,256,185  6/1966  LeSuer .............................. 252/47.5

Primary Examiner—Paul M. Coughlan, Jr.
Assistant Examiner—D. B. Springer
Attorney, Agent, or Firm—Carl G. Ries; Robert A. Kulason

[57] ABSTRACT

Disclosed are the preparation and use of thioureas derived from hydrocarbyl succinimides which have the formula:

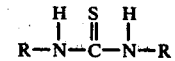

wherein R is a hydrocarbyl succinimide residue or hydrogen, with the proviso that only one R can be hydrogen. These thioureas offer superior performance over their parent succinimides in the areas of gasoline and diesel engine dispersancy, oxidation stability and friction modification.

3 Claims, No Drawings

PREPARATION FOR USE AS LUBE OIL ADDITIVES OF THIOUREAS CONTAINING N-POLYALKYLENEAMINO HYDROCARBYL SUCCINIMIDO GROUPS

FIELD OF THE INVENTION

The invention relates to sulfur-and nitrogen-containing compositions adapted for use as additives in hydrocarbon oils. More particularly, the invention concerns processes for making additives suitable as detergent-dispersants and additives made thereby.

STATEMENT OF PRIOR DISCLOSURES

There are numerous patents on the preparation and use of ashless additives of the present type. This background disclosure consequently is restricted to those which are believed most relevant.

Very basic in U.S. Pat. No. 3,256,185 which describes sulfur-and nitrogen-containing lubricant additives made by reacting alkylene amines, carbon disulfide and a hydrocarbon-substituted aliphatic dicarboxylic acid anhydride.

U.S. Pat. No. 3,331,776 is pertinent for disclosing lubricant detergents consisting of monoesters of a mono substituted polyolefin succinic anhydride and an alkanepolyol.

U.S. Pat. No. 3,381,022 is pertinent for disclosing esters of hydrocarbon-substituted succinic acid useful as detergents and emulsifiers in lubricating compositions.

U.S. Pat. No. 3,200,107 describes sulfur-and-nitrogen-containing lube oil additives prepared by heating an alkylene amine with a hydrocarbon-substituted dicarboxylic acid or anhydride and carbon disulfide.

U.S. Pat. Nos. 3,381,022 and 3,272,746 also relate to detergent-dispersants of interest.

As will be seen hereinafter, none of these disclose, hint or suggest in any manner whatsoever, applicant's novel, unique and unobvious process and products.

SUMMARY OF THE INVENTION

In accordance with this invention there are provided detergent-dispersants for lubricating oils which are defined by the general formula:

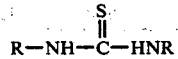

wherein R is a hydrocarbon-substituted dicarboxylic residue or hydrogen, except that only one R can be hydrogen.

Although the exact nature and distribution of the products have not been established, various physical properties such as %N, %S, Total Base Number, Infrared Spectra and proton and C-13 nuclear magnetic resonance substantiate the above theoretical general formula. In addition, model studies with octyl succinic anhydride imides were performed to verify structures.

The precise nature of the compounds depends on the actual method of preparation used and mixtures of compounds encompassed by the above formula may occur. However, both single compounds and mixtures are contemplated as being within the scope of this invention.

The preparation of these compounds is relatively uncomplicated and can be economically conducted. The reaction is facilitated by the use of a solvent for the reactants which is inert to the reaction and to the reaction products. A preferred solvent is mineral oil.

Generally, the subject additives are prepared by reacting thiourea or carbon disulfide with an alkyl or alkenylsuccinic anhydride and a polyamine in a mineral oil solvent in the presence of aqueous ammonia or of aqueous potassium hydroxide where $CS_2$ is used. The reaction produces in situ an alkenyl succinimide. The reaction can follow the routes shown below.

Method 1:

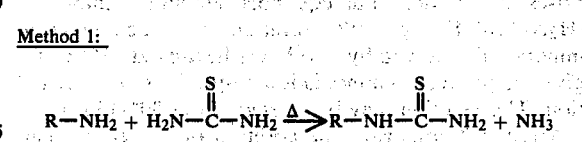

Method 2:

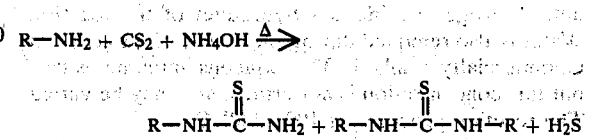

Method 3:

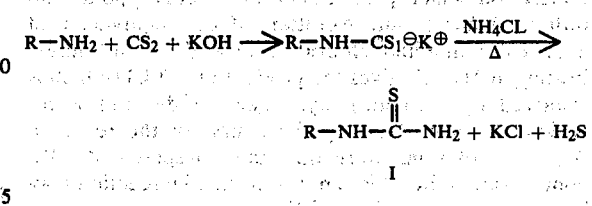

As above stated, R=H or a substantially hydrocarbon-substituted dicarboxylic acid imide residue, preferably, an alkyl or alkenylsuccinimide residue:

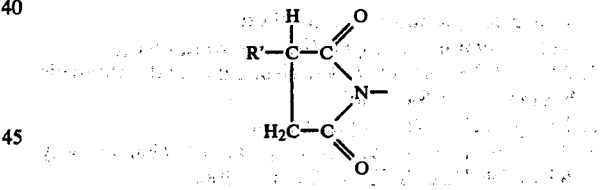

wherein R' is an alkyl or alkenyl radical having at least about 12 aliphatic carbon atoms.

The substantially hydrocarbon-substituted dicarboxylic anhydrides useful herein comprise principally the substituted succinic anhydrides although other dicarboxylic anhydrides such as substituted malonic, acids, glutaric acids, adipic acids, etc. likewise are contemplated for use herein. The substantially hydrocarbon radical in such anhydrides should contain at least about 12 aliphatic carbon atoms in order to impart sufficient oil solubility. It may also contain one or more inert polar substituents such as chloro, bromo, nitro, alkoxy, or phenoxy radical. The polyamines used are those conforming for the most part to the structure:

in which n is an integer preferably less than about 8. The alkylene amines include, for example, ethylene amine, propylene amines, butylene amines, trimethylene amine, tetramethylene amines, and also the cyclic homologues of such polyamines e.g., piperazines. Specific examples of the alkylene amines are ethylene diamine, diethylene triamine, triethylene tetramine, propylene diamine, tripropylene tetramine, tetraethylene pentamine, trimethylene diamine, pentaethylene tetramine, di(trimethylene) triamine, N-2 aminoethyl-piperazine, octamethylene diamine, etc. The ethylene amines are especially useful.

Referring to the above equations, Method 1 comprises the addition of an equimolar amount of thiourea, ($H_2NC(S)NH_2$) to a 50% solution of a succinimide in mineral oil followed by two hours heating at 125° C. to give the product. Ammonia is a by-product of the reaction. The reaction may be carried out at 80°–130° C.

Method 2 comprises the addition of one equivalent each of carbon disulfide and aqueous ammonia to a 50% solution of a polyalkenyl succinimide in mineral oil followed by two hours heating at 160° to give the product. Hydrogen sulfide is a byproduct of the reaction. Water is also removed during the course of the reaction. Commercially available 30% aqueous ammonia is used but this concentration is not critical and may be varied. The reaction proceeds at 100°–200° C.

Method 3 comprises the addition of one equivalent each of carbon disulfide and aqueous potassium hydroxide to a 50% solution of polyalkenyl succinimide in mineral oil which produces an intermediate potassium dithiocarbamate salt. Addition of one equivalent of aqueous ammonium chloride followed by two hours heating at 160° C. gives the product plus KCl (which is removed by filtration), hydrogen sulfide, and water which is removed during the course of the reaction. Aqueous solutions were nominally prepared at 50% concentration, but this is not critical. The reaction may be carried out at 100°–200° C.

The invention is described in non-limiting fashion by the following examples:

EXAMPLE I

This Example illustrates Method 1.
This Example employed the following charge:
1. 240 g, H-300 ASAA (alkenylsuccinic acid anhydride having a 56.5 Sap. No).
2. 16.5 g, TETA (triethylenetetramine).
3. 264.5 g(B) an oil having a sp. gr. of 0.88, Gravity API=29; Visc. SUS at 100° F.=100.
4. 9.5 g, Thiourea.

The TETA and oil B were charged to a reactor and stirred together until dissolved. The ASAA was warmed to 50°–60° C. to decrease viscosity and was added in one portion to the amine solution. The mixture was then heated to 160° C. using a nitrogen purge and Dean-Stark trap to collect water. A total of 1.7 ml of water was collected. After two hours at 160° C. heating was stopped and the reaction mixture cooled to 115° C. An aliquot of the reaction mixture was removed during cooling for subsequent analysis. Thiourea was then added in one portion to the reaction mixture and the temperature maintained at 125° C., with a nitrogen purge to remove ammonia. After 3 hours at 125° C. the product was filtered. Typical analyses for the product are as follows:

%N (Dohrman Method): 1.0
%N (Kjeldahl Method): 1.1
%S: 0.28
TBN (Total Base Number): 16

IR—essentially identical to that of the alkenyl succinimide of triethylenetetraamine.

EXAMPLE II

This Example illustrates Method 2.
The charge used here included:
1. 250 g. H-300 ASAA (56.5 Sap. No.)
2. 16.5 g. TETA
3. 264.5 g. mineral oil (B)
4. 9.5 g. carbon disulfide
5. 14.2 g. 30% Ammonium hydroxide The TETA and the oil B were charged to a reactor and stirred together until dissolved. The ASAA was warmed to 50°–60° C. to decrease viscosity and was added in one portion to the amine solution. The mixture was then heated to 160° C. using a nitrogen purge and Dean-Stark trap to collect water. A total of 1.7 ml of water was collected. After 2 hours at 160° C. heating was stopped and the reaction mixture cooled to 100° C. An aliquot of the reaction mixture was removed during cooling for subsequent analysis. A solution of carbon disulfide and ammonium hydroxide was prepared at ambient temperature and added in one portion to the reaction mixture at 100° C. The mixture was stirred together and the temperature raised to 160° C., using a nitrogen purge to remove hydrogen sulfide gas and water. After 2 hours at 160° C. the product was filtered. Typical analyses for the product are as follows:

%N (Dohrman): 0.90,0.95
%N (Kjeldahl): 1.05,1.10
%S: 0.35,0.41
$H_2O$: less than 0.05
TBN: 14,16

Ir essentially identical to that of the alkenylsuccinimide of triethylenetetraamine Selected physical properties for the product of Examples 1 to 3 are given below.

| Example | % N | % S | Total Base Number Found | Theory |
|---|---|---|---|---|
| 1 | 1.00 | 0.21 | 12.0 | 12.4 |
| 2 | 0.78 | 0.35 | 11.3 | 12.5 |
| 3 | 0.77 | 0.34 | 12.7 | 12.4 |

The following data demonstrates an increase in %N over the starting succinimides, indicating that products such as I in the above reaction scheme rather than II are being formed. In product II, the %N would be expected to decrease versus the starting materials.

| Example I | | 1 |
|---|---|---|
| Starting succinimide | % N(Dohrman Method) | 0.94 |
| | % N(Kjeldahl Method) | 0.985 |
| Product | % N(Dohrman) | 1.0 |
| | % N(Kjeldahl) | 1.1 |

Model studies done with n-octyl succinic anhydride (OSA) also support thiourea formation. The succinimide prepared from OSA and triethylenetetramine can be derivatized via methods 1–3. Analytical results of the products from methods 1 and 2 are consistent with the following structure:

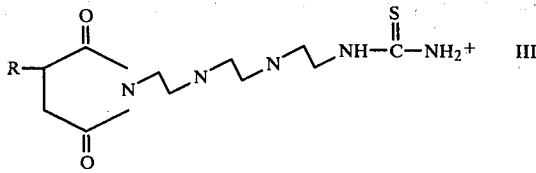

R = n-octyl

Analytical results for III

|  | Found | Theory |
|---|---|---|
| % N | 14.72 | 13.25[1] |
| % S | 6.65 | 6.05[1] |
| N/S | 5.05 | 5.0 |
| Total Base Number | 230 | 212 |
| C-13 NMR (C = 5) | 183.8 | 180–190[2] |

[1] Based on purity of anhydride
[2] Interpretation of Carbon-13 NMR Spectra, F. W. Wherli and T. Wirthlin, Heyden and Son, Ltd., London, 1976.

Based upon these results, it is likely that analogous thioureas are formed by reaction of the parent succinimide.

The compounds of the invention are incorporated in oils in an amount ranging from 0.2 to 75.0 weight percent of the final additive concentrate or lubricant formulation.

The suitability of representative compounds of the invention as multipurpose additives for lubricants was evaluated by several tests.

The products of the above examples were blended into automotive oil compositions and tested by various tests. Of these, the Bench VC Test, measures the turbidity of a degraded oil, the lower the turbidity values determined the better dispersancy. This test is carried out by mixing together exact volumes of the test oil, a synthetic blowby, and a mineral oil diluent in a test bottle. The bottle is then placed on a rocker and rocked for four hours at 280° F. After heating, the sample is diluted with more mineral oil, cooled to room temperature, and the sample's turbidity is measured with a Lumetron turbidimeter equipped with a 700 millimicron filter. Synthetic blowby is a hydrocarbon fraction which has been oxidized under specific conditions. This material emulates the oxidized compounds which find their way past the piston rings and into the crankcase of an internal combustion engine.

The Bench L-38 Test simulates the engine test environment of Federal Test Method No. 791a, Method 3405.1, and provides a method for studying the copper-lead bearing corrosion characteristics of crankcase oils. In carrying out this test a journal bearing is rotated in a journal bearing rig, (JBR), which contains a pre-weighed connecting rod bearing along with 500 ml. of test oil. The oil is heated to 200° F. and the journal rotated at 1725 RPM for 2 hours, an activator is added and the temperature increased to 305° F. for 22 hours. The bearings are then removed, cleaned with pentane and reweighed. The difference in weight is then reported as the bearing wt. loss (BWL) in mg.

The third test employed was the Four Ball Wear Test described in U.S. Pat. No. 3,384,588 which measures the amount of wear a lubricating oil permits under engine test conditions with and without additives to be tested. The greater amount of wear, the poorer the ability of the test oil composition to prevent such wear. This wear is measured in terms of millimeter wear scar diameter. This test was run for 1 hour at 600 rpm/200° F./40 kg load. The friction coefficient was measured at the end of the test when the anti-friction film is fully developed.

The Small Engine Friction Test is a single cylinder engine test which measures the frictional characteristics of an oil. These frictional results are integrated with high shear rate viscosity measurements of viscosity and additives on friction levels. The values given in Table I are based on the torque required to motor an engine containing the oil under test. The results of this test have been found to correlate with field experience using a large fleet of cars under varied on-the-road driving conditions as the percentage change in torque correlates with a percent change in fuel economy.

The Sequence IID is described in ASTM Special Technical Publication No. 315H and evaluates motor oils with respect to low temperature rusting in an engine operated continuously for 28 hours at moderate speed and for a final four hours at higher temperature. The engine is disassembled and visually inspected for lifter, push rod and oil pump relief valve rust.

The Caterpillar 1-G test (PTMS 791b-341) is described in U.S. Army Reviewing Committee Information Letter No. 80. This test evaluates the diesel detergency characteristics and anti-wear properties of diesel crankcase oils under high speed supercharged test condition. The test equipment comprises a 1Y73 single cylinder Caterpillar Diesel Lubricants Test Engine. The performance of the test lubricant is judged by examination of the power section for ring sticking, piston deposits and ring, piston and liner wear.

Thioureas prepared by methods 1–3 show superior dispersancy over the parent alkenylsuccinimide as measured by the Bench VC Test. These results, compared with those from the succinimide are presented below.

|  | Bench VC Results[1] | |
|---|---|---|
| Dispersant | 4%[2] | 6%[2] |
| Thioureas | 20.3 | 9.2 |
| Parent alkenylsuccinimide | 32.0 | 10.3 |

[1] Reference results were 2.5, 17.0, and 67.5 for FREO 126,127 and 179 respectively.
[2] As a 50—50 concentrate in mineral oil.

In the Caterpillar 1-G2 diesel engine test, the thiourea from method 2 was equivalent to the parent succinimide, giving 120-hour results of %TGF, 62 and WTD, 233, in the following blend:

62.24% Solvent Neutral Oil, 28,00% Solvent neutral oil (Sp. Gr. 0.88 to 0.89), 5.5% thiourea (as a 50-50 oil concentrate), 0.80% zinc dialkyldithiophosphate, 1.08% calcium phenate, 1.83% diisodecyl zinc dithiophosphate, 0.25% 4.4 dinonyldiphenylamine, 0.25% of nonylphenol ethoxylated with 6 moles of ethylene oxide, 0.05% pour dispersant and 150 ppm antifoam agent.

The parent succinimide gave: %TGF 67.5 WTD 300 in a similar blend.

The same thiourea (Ex. 2) showed friction modifying ability as measured in the 4-Ball Friction and Wear Test and the Small Engine Friction Test. It also proved equivalent to the parent succinimide in corrosion resistance (as measured in the L-38 Test) and in rust protection (as measured by the Sequence II-D Test). The results are presented in Table 1.

TABLE I

|  | Results | |
|---|---|---|
| Test | Exp. thiourea | Parent succinimide |
| 4-Ball Friction | | |

TABLE I-continued

| Test | Results | |
|---|---|---|
| | Exp. thiourea | Parent succinimide |
| and Wear[1] | | |
| Coefficient of Friction | 0.049 | 0.115 |
| Wear | 0.41 | 0.47 |
| Small Engine Friction Test[2] | | |
| Engine Motoring Torque, Ft.-Lbs. | Temp. | |
| | 130  2.42 | 2.57 |
| | 160  2.33 | 2.31 |
| | 190  2.21 | 2.24 |
| | 220  2.17 | 2.22 |
| | 250  2.17 | 2.34 |
| | 280  2.20 | 2.45 |
| L-38 Test[2] | | |
| bwl (mg) | 36.3 | 44.1 |
| Sequ. II-D Test[2] | | |
| ARR | 7.6 | 7.9 |

[1]55 wt. % of a 50—50 concentrate blended in a fully formulated 10W-40 oil.
[2]4.0 wt. % of a 50—50 concentrate blended in a low-ash, low-phosphorus package.

The thioureas have also shown oxidation stability as measured by the Bench III D Test. These results are presented below in Table II.

TABLE II

| Kinetic | Hrs. | Thiourea[1] | Succinimide[1] |
|---|---|---|---|
| Viscosity | 0 | 88.7 | 89.6 |
| | 24 | 92.4 | 107.6 |
| | 48 | 124.4 | 107.6 |
| | 72 | 139.2 | 169.4 |
| | 0 | 90.8[2] | 91.3[2] |
| | 24 | 111.5 | 119.6 |
| | 48 | 116.4 | 112.9 |
| | 72 | 149.3 | 185.1 |

[1]3 wt. % dispersant.
[2]Fully formulated 10W-40 oil with 4,4 dinonyldiphenylamine It is important to note that in both cases at 72 hours the blends containing thioureas had significantly lower kinetic viscosity indicating increased oxidation protection.

What is claimed is:

1. A compound of the formula:

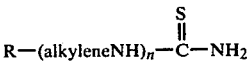

wherein R is the succinimide residue

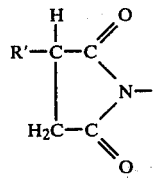

in which R' is an alkyl or alkenyl residue having more than 8 carbon atoms; and n is an integer from 2 to 8, prepared by heating to 80° to 130° C. a reaction mixture of an alkyl or alkenylsuccinic anhydride and a polyalkylene amine terminated by two primary amino groups using half of the equimolecular amount of amine per equivalent of anhydride to form a succinimide; removing water; cooling said reaction mixture; adding thiourea; heating said mixture; purging ammonia formed with an inert gas and isolating a product having the above formula.

2. The compound of claim 1, wherein R is an n-tetradecenyl succinimide residue.

3. The compound of claim 1, wherein R is an octyl succinimide residue.

* * * * *